United States Patent [19]

Schönafinger et al.

[11] Patent Number: 4,880,818
[45] Date of Patent: Nov. 14, 1989

[54] 1-ACYL-4-[1-(4-QUINOLINYL)-HYDRAZIN-2-YLIDENE]PIPERIDINES AND THEIR USE AS HYPOTENSIVE AGENTS

[75] Inventors: Karl Schönafinger, Alzenau, Fed. Rep. of Germany; Helen Hu Ong, Whippany, N.J.

[73] Assignee: Hoechst-Roussel Pharmaceuticals, Inc., Somerville, N.J.

[21] Appl. No.: 218,749

[22] Filed: Jul. 12, 1988

Related U.S. Application Data

[62] Division of Ser. No. 12,715, Feb. 5, 1987, Pat. No. 4,771,052.

[51] Int. Cl.$^4$ .................... A61K 31/47; C07D 401/12
[52] U.S. Cl. .................... 514/313; 514/287; 546/64; 546/162
[58] Field of Search .................... 546/162; 514/313

[56] References Cited

U.S. PATENT DOCUMENTS

3,152,133 10/1964 Lowrie .................... 546/162
3,646,019 2/1972 Actor et al. .................... 546/162

OTHER PUBLICATIONS

Mann et al., *Chemical Abstracts*, vol. 54, No. 7706d, f and g (1960).
*Medicinal Chemistry*, (2nd. ed.) Burger, editor, Interscience Publ., pp. 42–43 (1960).

Primary Examiner—Mukund J. Shah
Assistant Examiner—E. Bernhardt
Attorney, Agent, or Firm—Tatsuya Ikeda

[57] ABSTRACT

There are disclosed compounds of the formula

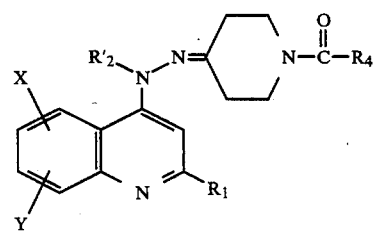

where X,Y are each independently hydrogen, loweralkyl, loweralkoxy, hydroxy, halogen, trifluoromethyl or nitro; $R_1$ is hydrogen or loweralkyl; $R_2'$ is hydrogen or loweralkyl and $R_4$ is hydrogen, loweralkyl or aryl, which are useful as hypotensive agents and as intermediates.

6 Claims, No Drawings

1-ACYL-4-[1-(4-QUINOLINYL)-HYDRAZIN-2-YLIDENE]PIPERIDINES AND THEIR USE AS HYPOTENSIVE AGENTS

This is a division of application Ser. No. 012,715, filed Feb. 5, 1987, now U.S. Pat. No. 4,771,052.

The present invention relates to compounds of formula I

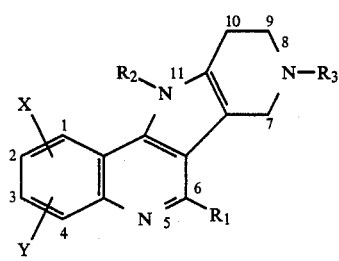

where X and Y are independently hydrogen, loweralkyl, loweralkoxy, hydroxy, halogen, trifluromethyl or nitro; $R_1$ is hydrogen or loweralkyl; $R_2$ is hydrogen, loweralkyl, loweralkylcarbonyl or arylcarbonyl; and $R_3$ is hydrogen, loweralkyl, arylloweralkyl,

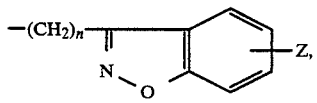

loweralkylcarbonyl or arylcarbonyl, n being an interger of 1 to 6 inclusive and Z being hydrogen, loweralkyl, loweralkoxy, hydroxy or halogen, and pharmaceutically acceptable acid addition salts thereof, which are useful as hypotensive agents; pharmaceutical compositions comprising an effective amount of such a compound; method of treating a patient in need of blood pressure lowering which comprises administration of such a compound to the patient and methods of synthesizing such compounds.

The present invention also relates to compounds of formula II

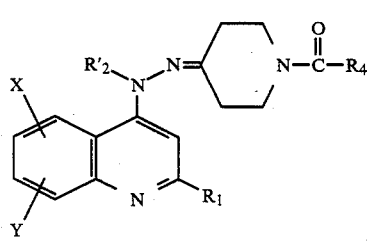

where X, Y, and $R_1$ are as defined above and $R_2'$ is hydrogen or loweralkyl and $R_4$ is hydrogen, loweralkyl or aryl, which are useful as hypotensive agents and as intermediates for synthesizing the above-mentioned compounds of formula I.

Throughout the specification and the appended claims, a given chemical formula or name shall encompass all stereo, optical and geometrical isomers thereof where such isomers exist, as well as pharmaceutically acceptable acid addition salts thereof and solvates thereof such as for instance hydrates.

The following general rules of terminology shall apply throughout the specification and the appended claims.

Unless otherwise stated or indicated, the term loweralkyl denotes a straight or branched alkyl group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term halogen shall mean fluorine, chlorine, bromine or iodine.

Unless other wise stated or indicated, the term aryl shall mean a phenyl group having 0, 1, 2 or 3 substituents each of which being independently hydroxy, nitro, loweralkyl, loweralkoxy, halogen or $CF_3$.

The compounds of formula I and formula II are prepared by utilizing one or more of the reaction steps described below. Throughout the description of the synthetic steps, the definitions of X, Y, Z, $R_1$, $R_2$, $R_2'$, $R_3$, $R_4$ and n are as given above unless otherwise stated or indicated, and other nomenclatures shall have their respective definitions given at their first appearances unless otherwise stated or indicated.

STEP A

A compound of formula III is reacted with a compound of the formula IV in a routine manner known to the art to obtain a compound of formula V.

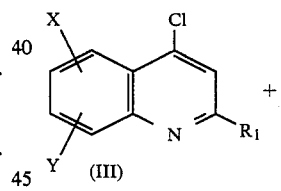

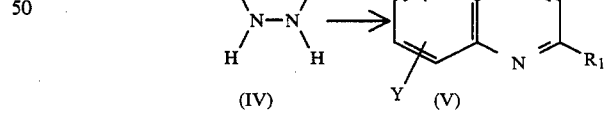

STEP B

Compound V is reacted with a compound of formula VI to afford a compound of formula VII.

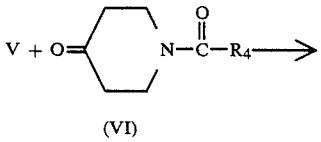

-continued

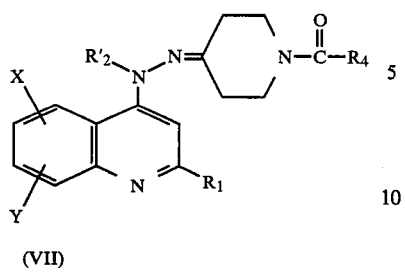

(VII)

The above reaction is typically conducted in a suitable solvent, for instance, loweralkanol (such as methanol and ethanol), diethyleneglycol or ethoxyethanol at a temperature of about 0° C.–140° C.

STEP C

Compound VII is cyclized to afford a compound of formula VIII.

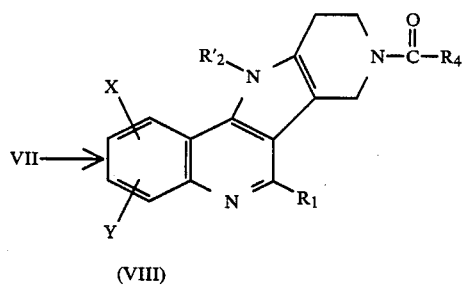

(VIII)

The above cyclization is typically conducted in a suitable solvent such as dimethyleneglycol, or trimethyleneglycol at a temperature of about 150°–200° C. Reflux condition is preferred.

STEP D

Compound VIII is hydrolyzed to afford a compound of formula VIII.

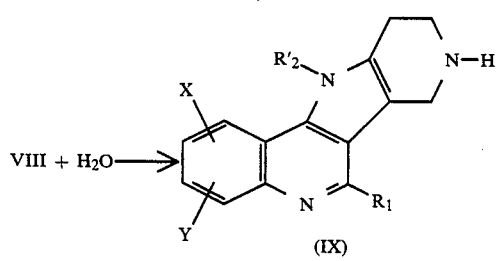

(IX)

The above hydrolysis is typically conducted in concentrated hydrochloric acid at a temperature of about 20°–100° C., preferably under reflux.

STEP E

Compound IX is reacted with a compound of the formula $R_5$-Hal where Hal is chlorine, bromine, iodine or fluorine and $R_5$ is loweralkyl, arylloweralkyl

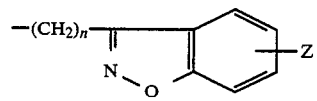

or to afford a compound of formula X.

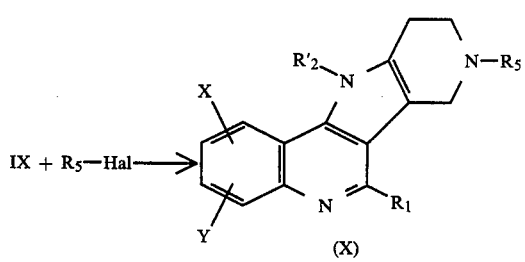

(X)

The above reaction is typically conducted in a suitable solvent such as N,N-dimethylformamide, tetrahydrofuran or toluene and in the presence of an acid scavenger such as powdered $K_2CO_3$ or $Na_2CO_3$ at a temperature of about 20°–130° C.

STEP F

As an alternative to STEP E, compound IX is reacted with paraformaldehyde and formic acid to afford a methyl substituted compound of formula XI.

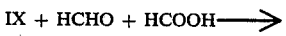

IX + HCHO + HCOOH ⟶

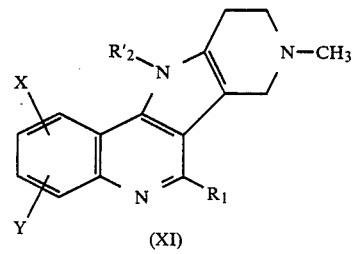

(XI)

The above reaction is typically conducted by preparing a suitable mixture of compound X, paraformaldehyde and formic acid and heating it at a temperature of about 40°–80° C.

STEP G

A compound of formula XI obtained from one of the foregoing steps is reacted with a compound of the formula $R_6$-CO-Cl where $R_6$ is loweralkyl or aryl in a routine manner known to the art to afford a compound of formula XII.

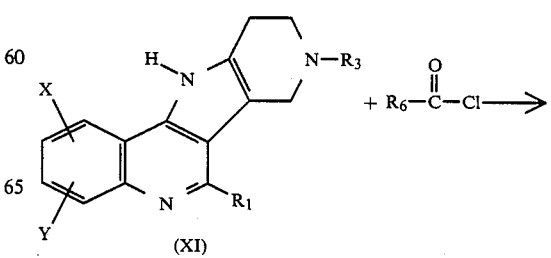

(XI)

-continued

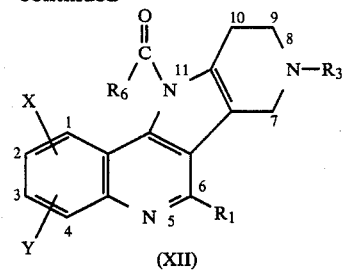

The compounds of formulas I and II of the present invention are useful as antihypertensive agents due to their ability to depress blood pressure in mammals. Antihypertensive activity is measured in the spontaneous hypertensive rat by the indirect tail cuff method described in "Methods in Pharmacology", A. Schwartz, Ed., Vol. I, Appleton-Century Crofts, New York, N.Y., 1971, p. 135. In this procedure a group of five animals are treated orally for three days with the test compound in relation to a control group of the same number. The drop in blood pressure is measured on the third day following administration. The antihypertensive activities of some of the compounds, expressed as a decrease in systolic pressure (in mmHg), are given in Table I.

TABLE I

| Antihypertensive Activity | | |
|---|---|---|
| Compound | Pressure drop (mmHg) | Dose (mg/kg, p.o.) |
| 8-Acetyl-3-chloro-11-methyl-7,8,9,10-tetrahydro-pyrido[3',4':4,5]pyrrolo[2,3-c]quinoline | 37 | 50 |
|  | 48 | 30 |
|  | 61 | 10 |
| 1-Acetyl-4-[1-(7-chloro-4-quinolinyl)-hydrazino-2-ylidene]-piperidine (Prior Art Compound) | 57 | 50 |
| alpha-Methyldopa | 40 | 50 |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base of final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acid.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain perservatives, dyes, coloring and flavors. used in preparing these various compositions should be pharmaceutically pure and non-toxic in the amounts used.

For the purpose of parenteral therapeutic administration, the active compounds of the invention may be incorporated into a solution of suspension. These preparations should contain at least 0.1% of active compound, but may be varied between 0.5 and about 30% of the weight thereof. The amount of active compound in such compositions is such that a suitable dosage will be obtained. Preferred compositions and preparations according the the present invention are prepared so that a parenteral dosage unit contains between 0.5 and 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral multiple dose vials made of glass or plastic.

Examples of the compounds of this invention include:
1-acetyl-4-[1-(7-chloro-4-quinolinyl)-hydrazino-2-ylidene]-piperidine;
8-acetyl-3-chloro-7,8,9,10-tetrahydro-11H-pyrido[3',4':4,5]pyrrolo[2,3-c]quinoline;
8-acetyl-7,8,9,10-tetrahydro-11H-pyrido[3',4':4,5]pyrrolo[2,3-c]quinoline;
8-acetyl-3-chloro-11-methyl-7,8,9,10-tetrahydro-pyrido[3',4':4,5]pyrrolo[2,3-c]quinoline;
3-chloro-7,8,9,10-tetrahydro-11H-pyrido[3',4':4,5]pyrrolo[2,3-c]quinoline;
3-chloro-8-[3(6-fluorobenzisoxazol-3-yl)propyl]-7,8,9,10-tetrahydro-11H-pyrido[3',4':4,5]pyrrolo[2,3-c]quinoline;
3-chloro-11-methyl-7,8,9,10-tetrahydro-pyrido[3',4':4,5]pyrrolo[2,3-c]quinoline;

3-chloro-8-methyl-7,8,9,10-tetrahydro-11H-pyrido[3',4':4,5]pyrrolo[2,3-c]quinoline; and 3-chloro-8,11-dimethyl-7,8,9,10-tetrahydro-pyrido[3',4':4,5]pyrrolo[2,3-c]quinoline.

The following examples are presented for the purpose of illustrating this invention.

EXAMPLE 1

1-Acetyl-4-[1-(7-chloro-4-quinolinyl)-hydrazino-2-ylidene]piperidine

A solution prepared from 46 g of 7-chloro-4-hydrazinoquinoline, 33.6 g of N-acetyl-4-piperidone and 200 ml of ethanol was stirred at room temperature for 2 days and then diluted with 500 ml of water. The resultant solid was filtered and recrystallized from ethanol. The yield was 55 g, mp=153°–154° C.

ANALYSIS: Calculated for $C_{16}H_{17}ClN_4O$: 60.66%C, 5.41%H, 17.69%N. Found: 60.51%C, 5.25%H, 17.39%N.

EXAMPLE 2

8-Acetyl-3-chloro-7,8,9,10-tetrahydro-11H-pyrido[3',4':4,5]pyrrolo[2,3-c]quinoline A solution prepared from 10 g of the crude 1-acetyl-4-[1-(7-chloro-4-quinolinyl)-hydrazino-2-ylidene]piperidine obtained in Example 1 and 20 ml of diethyleneglycol was heated at 220° C. (reflux) for 1 hour. The mixture was diluted with water (200 ml) and stirred for 2 hours. The resultant solid was filtrated, recrystallized from ethoxyethanol and washed with ethanol. The yield was 5.0 g, mp =235°–237° C.

ANALYSIS: Calculated for $C_{16}H_{14}ClN_3O$: =64.11%C, 4.67%H, 14.02%N. Found: 64.08%C, 4.79%H, 14.03%N.

EXAMPLE 3

8-Acetyl-7,8,9,10-tetrahydro-11H-pyrido[3',4':4,5]pyrrolo[2,3-c]quinoline

A mixture of 10 g of 4-hydrazinoquinoline and 8.15 g of N-acetyl-4-piperidone in diethyleneglycol was stirred at 190°–210° C. for 2 hours. The reaction was complete after this time as shown by thin layer chromatography. Quenching was done with ice-water and the organics were extracted with dichloromethane. Evaporation of solvents resulted in a solid which was recrystallized from isopropanol to yield 8.4 g of a compound with a melting point of 218°–221° C.

ANALYSIS: Calculated for $C_{17}H_{17}N_3O$: 73.09%C, 6.14%H, 15.04%N. Found: 73.06%C, 5.98%H, 15.16%N.

EXAMPLE 4

8-Acetyl-3-chloro-11-methyl-7,8,9,10-tetrahydro-pyrido[3',4':4,5]pyrrolo[2,3-c]quinoline A mixture prepared from 7 g of 7-chloro-4-(1-methyl-hydrazino)quinoline hydrochloride, 4.1 g of N-acetyl-4-piperidone, 3 g of sodium carbonate and 50 ml of methanol was heated at 70° C. for 30 minutes. The mixture was allowed to cool and thereafter filtered. The filtered solution was concentrated and the oily residue heated in 30 ml of diethyleneglycol at 180° C. for 30 minutes. The mixture while still hot was poured into 200 ml of ice water. The solid which formed after stirring was filtered and recrystallized from isopropanol and from ethanol. The yield was 3.5 g, mp =299° C. (decomposition).

ANALYSIS: Calculated for $C_{17}H_{16}ClN_3O$: 65.07%C, 5.10%H, 13.40%N. Found: 65.03%C, 5.17%H, 13.47%N.

EXAMPLE 5

3-Chloro-7,8,9,10-tetrahydro-11H-pyrido[3',4':4,5z-]pyrrolo[2,3-c]quinoline

A mixture prepared from 27 g of 8-acetyl-3-chloro-7,8,9,10-tetrahydro-11H-pyrido[3',4':4,5]pyrrolo[2,3-c]quinoline and 200 ml of concentrated hydrochloric acid was heated at reflux for 1 hour, whereupon a solid precipitated. The mixture was stirred overnight at room temperature, and the solid was filtrated and dissolved in 200 ml of water. This solution was made alkaline with 25% sodium hydroxide solution, and the solid-form free base was filtrated and washed with ethanol. The yield was 17 g, mp=285° C. (dec).

ANALYSIS: Calculated for $C_{14}H_{12}ClN_3$: 65.24%C, 4.66%H, 16.31%N. Found: 65.07%C, 4.80%H, 16.20%N.

EXAMPLE 6

3-Chloro-8-[3-(6-fluorobenzisoxazol-3-yl)propyl]-7,8,9,10-tetrahydro-11H-pyrido[3',4':4,5]pyrrolo[2,3-c]quinoline A mixture prepared from 5.15 g of 3-chloro-7,8,9,10-tetrahydro-11H-pyrido[3',4':4,5]pyrrolo[2,3-c]quinoline, 7.0 g of 3-(3-chloropropyl)-6-fluorobenzisoxazole, 4.0 g of potassium carbonate (powdered) and 30 ml of N,N-dimethylformamide was stirred at 100° C. for 2 hours. The mixture was diluted with 150 ml of water and the oily precipitate was purified by high performance liquid chromatography (HPLC) using dichloromethane/methanol mixtures of 95:5 and 10:1 ratios. The clean fractions were combined and concentrated. The residue was stirred in isopropanol and filtered. The yield was 1.2 g, mp=221°–222° C.

ANALYSIS; Calculated for $C_{24}H_{20}ClFN_4O$: 66.28%C, 4.64%H, 12.88%N. Found: 66.63%C, 4.79%H, 12.74%N.

EXAMPLE 7

3-Chloro-11-methyl-7,8,9,10-tetrahydro-pyrido[3',4':4,5]pyrrolo[2,3-c]quinoline A mixture prepared from 17.5 g of 8-acetyl-3-chloro-11-methyl-7,8,9,10-tetrahydro-pyrido[3',4':4,5]pyrrolo[2,3-c]quinoline and 125 ml of concentrated hydrochloric acid was refluxed for one hour. The product precipitated as hydrochloride salt and it was recovered by filtration. The salt was suspended in water and the mixture was basified with 50% sodium hydroxide solution. The resultant solid was recovered by filtration and recrystallized from isopropanol to give 11 g of crystalline solid with a melting point of 209°–212° C.

ANALYSIS: Calculated for $C_{15}H_{14}ClN_3$: 66.30%C, 5.19%H, 15.46%N. Found: 66.01%C, 5.07%H, 15.29%N.

EXAMPLE 8

3-Chloro-8-methyl-7,8,9,10-tetrahydro-11H-pyrido[3',4':4,5]pyrrolo[2,3-c]quinoline A mixture prepared from 3.7 g of 3-chloro-7,8,9,10-tetrahydro-11H-pyrido[3',4':4,5]pyrrolo[2,3-c]quinoline, 0.45 g of paraformaladehyde and 100 ml of formic acid was heated at 90° C. for one hour. The reaction was quenched with water and the solution was made alkaline (pH9) with a sodium hydroxide solution. The crystalline product was filtered, washed with water and purified by HPLC using dichloromethane/methanol=8:2 as an eluent. Clean fractions were combined and concentrated, and the crystalline residue was stirred in isopropanol and filtered. The yield was 2.1 g, mp=286°–287° C.

ANALYSIS: Calculated for $C_{15}H_{14}ClN_3$: 66.30%C, 5.19%H, 15.46%N. Found: 66.28%C, 5.20%H, 15.59%N.

EXAMPLE 9

3-Chloro-8,11-dimethyl-7,8,9,10-tetrahydro-pyrido[3',4':4,5]pyrrolo[2,3-c]quinoline A solution prepared from 6 g of 3-chloro-11-methyl-7,8,9,10-tetrahydro-pyrido[3',4':4,5]pyrrolo[2,3-c]quinoline, ml of formic acid and 0.7 ml of formaldehyde was stirred at 90° C. for four hours. The mixture was cooled to room temperature and quenched with 50 ml of water. The mixture was basified with 25% sodium hydroxide solution, whereupon a solid precipitated, which was recovered by filtration and purified by HPLC using 10:1 dichloromethane/methanol as an eluent. Recrystallization from ethyl acetate resulted in 1.44 g of a solid with a melting point of 188°–190° C.

ANALYSIS: Calculated for $C_{16}H_{16}ClN_3$: 67.24%C, 5.64%H, 14.70%N. Found: 66.97%C, 5.41%H, 14.86%N.

We claim:

1. A compound of the formula

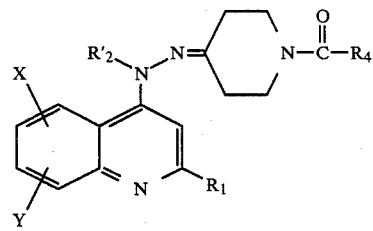

where X and Y are each independently hydrogen, loweralkyl, loweralkoxy, hydroxy, halogen, trifluoromethyl or nitro; $R_1$ is hydrogen or loweralkyl; $R_2'$ is hydrogen or loweralkyl; and $R_4$ is hydrogen, loweralkyl or aryl, the term aryl signifying a phenyl group optionally substituted with 1, 2 or 3 substituents each of which being independently hydroxy, nitro, loweralkyl, loweralkoxy, halogen or trifluoromethyl, with the proviso that the aryl does not include trinitrophenyl, triiodophenyl or trihydroxyphenyl, or a pharmaceutically acceptable acid addition salt thereof.

2. The compound as defined in claim 1, where $R_1$ is hydrogen.

3. The compound as defined in claim 1, where X is hydrogen.

4. The compound as defined in claim 3, where Y is hydrogen.

5. A hypotensive composition comprising an effective blood pressure lowering amount of the compounds as defined in claim 1 and a pharmaceutically acceptable carrier therefor.

6. A method of treating a patient in need of relief from high blood pressure which comprises administering to the patient an effective blood pressure lowering amount of the compound as defined in claim 1.

* * * * *